United States Patent [19]

Knighton

[11] Patent Number: 4,957,742

[45] Date of Patent: Sep. 18, 1990

[54] METHOD FOR PROMOTING HAIR GROWTH

[75] Inventor: David R. Knighton, Hudson, Wis.

[73] Assignee: Regents of the University of Minnesota, Minneapolis, Minn.

[21] Appl. No.: 295,406

[22] Filed: Jan. 10, 1989

Related U.S. Application Data

[63] Continuation-in-part of Ser. No. 39,776, Apr. 15, 1987, which is a continuation of Ser. No. 786,206, Oct. 10, 1985, abandoned, which is a continuation-in-part of Ser. No. 676,471, Nov. 29, 1984, abandoned.

[51] Int. Cl.$^5$ ............................................. A61K 35/14
[52] U.S. Cl. ...................................... 424/532; 514/2; 514/880
[58] Field of Search .................... 514/2, 880; 424/101

[56] References Cited

PUBLICATIONS

Scher et al.—Chem. Abst., vol. 102, (1985), p. 161,144q.

Primary Examiner—Sam Rosen
Attorney, Agent, or Firm—Dorsey & Whitney

[57] ABSTRACT

Platelet enriched plasma is produced from blood. The platelets are activated by thrombin which causes the release of platelet-derived growth and angiogenesis factors. A carrier such as a microcrystalline collagen is added to produce a wound-treating salve. The composition is applied directly to wounds and initiates healing in nonhealing wounds as well as accelerating normal wound-healing by increasing vascularization, stimulating fibroblast mitosis and migration, and increasing collagen synthesis by fibroblasts. The composition is also applied to tissue to facilitate the growth of hair.

11 Claims, No Drawings

METHOD FOR PROMOTING HAIR GROWTH

This application is a continuation in part of co-pending application Serial No. 39,776, filed Apr. 15, 1987, which was a file wrapper continuation of application Ser. No. 786,206, filed Oct. 10, 19B5. now abandoned, which was a continuation-in-part of application Ser. No. 676,471, filed Nov. 29, 1984, now abandoned.

FIELD OF THE INVENTION

This invention relates to wound-healing agents, specifically angiogenic and growth factors, their production from blood and their use to facilitate the healing of wounds and the growth of hair.

BACKGROUND OF THE INVENTION

Angiogenesis, which is the proliferation and directed growth of capillary endothelium, along with fibroplasia and collagen synthesis are integral components of a host's response to wounding. The activation of platelets and the clotting cascade are among the first reactions to injury.

Platelets activated by thrombin release a mitogen, or growth factor, for fibroblasts and smooth muscle cells and stimulate increased collagen synthesis by smooth muscle cells in vitro. The mitogen (platelet-derived growth factor, hereinafter PDGF) is composed of two polypeptides. An article describing PDGF was published in 1982 by G. R. Grotendorst, T. Chang, H. E. J. Seppa, H. K. Kleinman and G. R. Martin in the *Journal of Cellular Physiology* entitled "Platelet-Derived Growth Factor is a Chemoattractant for Vascular Smooth Muscle Cells", Vol. 113, pp. 261–266. The article is incorporated herein by reference.

A non-mitogenic substance, called angiogenic factor, is also produced by thrombin-activated platelets and stimulates capillary growth. Various angiogenesis factors are known including tumor, retinal and wound fluid angiogenesis factors. It is unknown whether all angiogenesis factors share a common mechanism of action upon capillary endothelial cells.

Angiogenesis factors were isolated and described *Proc. Nat'l Acad. Sci.* U.S.A. (7773–7777, Dec. 1982), in an article entitled "Isolation of a nonmitogenic angiogenesis factor from wound fluid," the disclosure of which is incorporated herein by reference.

Angiogenesis and platelet-derived growth factors are described by D. R. Knighton, T. K. Hunt, K. K. Thakral and W. H. Goodson III, in "Role of Platelets and Fibrin in the Healing Sequence", Annals of Surgery 196: 379–388 (1982), the disclosure of which is incorporated by reference. In this article, the successful treatment of a non healing wound in a patient is described in which a single, ten-unit platelet transfusion was given. The wound healed in three weeks.

A recent study has indicated that when the body's normal healing process works, it is only at about a 50% effectiveness level.

A human angiogenic factor is produced from human foreskin fibroblasts in U.S. Pat. No. 4,273,871 to Tolbert, et al. A publically available foreskin fibroblast cell line is utilized to produce an angiogenic factor.

In U.S. Pat. No. 4,479,896 to Antoniades, the disclosure of which is incorporated herein by reference, platelet derived growth factors are characterized and extracted for study by gel electrophoresis means.

BRIEF SUMMARY OF THE INVENTION

Thrombin-activated platelets have the capacity to stimulate angiogenesis, increased collagen synthesis and cell division and growth. It has been found that samples of whole blood may be utilized to prepare a platelet-enriched plasma, which, when activated by thrombin, contains angiogenic and growth factors which may be used to speed the healing process of wounds.

Blood is stabilized and centrifuged to obtain a platelet-rich plasma. The blood is stabilized by mixing with citrate-phosphate dextrose in a ratio of 1:5 (20% solution). The platelet-rich plasma (hereinafter, PRP) is preferably centrifuged again until a high concentration of platelets is obtained. The platelets are then placed in a platelet buffer. The concentration of platelets should be at least 1,000,000 platelets per milliliter. Preferably, the concentration should be on the order of 1,000,000,000 platelets per milliliter.

Thrombin is added to the PRP in order to activate the platelets. Preferably, about 1 to about 10 units of thrombin are utilized per milliliter of PRP. The thrombinactivated platelets release platelet derived growth factors (hereinafter, PDGF) and platelet derived angiogenesis factors (hereinafter, PDAF). The platelets and thrombin are allowed to incubate at room temperature for about 5 to 10 minutes.

The activated PRP containing PDGF and PDAF is preferably added to a biologically compatible macromolecular substance which acts as a carrier. First, the platelets are centrifuged at about 950 × g and the platelet-free supernatant is mixed with the carrier. Preferably, a microcrystalline collagen such as Aviteneg brand collagen as sold by FMC Corp., Avicel Dept., Marus Hook, PA 19061 is utilized as the biologically compatible carrier. Micro-crystalline collagens are biologically compatible in the body. Enough carrier is added to soak up all the platelet rich plasma that is obtained from the blood. For example, a 40 ml blood sample would typically require about 25 ml of carrier after enrichment. The paste so obtained is preferably stored on ice or in the refrigerator.

The pharmaceutical preparations for use as a wound dressing sold by Pharmacia Fine Chemicals, Inc. of Piscataway, N.J. under the trademark Debrisan is a suitable carrier.

The activated PRP within the carrier may then be applied to a wound. The highly enriched and active PDGF and PDAF therewithin assists in healing by proliferating and directing the growth of capillary endothelium, doubling the rate of collagen synthesis and by producing leukocyte chemotaxis. Mitogenic activity results in cellular division and growth to replace the lost tissue.

Daily application of the activated PRP to wounds stimulates and bolsters the healing sequence. The amount of PRP processed from 40 ml of blood is enough to produce applications for seven days. The material is placed over the entire wound at a relatively uniform thickness, approximately two millimeters thick. Granulation, contraction and epithelization may be initiated through the use of activated PRP where the body's own repair signals are inadequate to stimulate good healing.

Topical application of the compositions to areas of tissue containing hair follicles has also been found to promote hair growth where no growth or limited growth was previously observed.

DETAILED DESCRIPTION OF THE INVENTION

Blood obtained from the individual to be treated with the wound healing factors of the invention is stabilized in siliconized tubes containing acid citrate dextrose (0.15 M citrate, 2 % glucose, pH 4.2) (hereinafter, CPD) and is centrifuged in order to separate out the platelet-rich plasma therefrom. Forty to sixth milliliters of blood combined with 4-6 ml of CPD is then centrifuged at about 135 $\times$g for 20 minutes at about 4 C. to obtain platelet-rich plasma. The platelet rich plasma is removed and placed into another sterile 50 ml tube. A platelet count is then taken. The CDP is utilized to prevent activation of the clotting sequence by contact of the blood with the plastic in the syringe. The CPD is present in the syringe while the blood is withdrawn from the patient. The blood is continuously mixed with the CPD to prevent coagulation. The platelet-rich plasma in the tube is then centrifuged at 750 $\times$g for 10 minutes at 4 C.

The platelet-free plasma is removed and discarded. The platelet platellet is resuspended in a quantity of platelet buffer to produce a final ml. A lower concentration of about a million platelets per ml is useful, but is less preferred. The platelet buffer utilized contains 0.05 M HEPES (N-2-hydroxyethylpiperazine-n-2-ethanesulfonic acid), 0,03 M glucose, 0.004 M KCl, 0.1 M NaCl and about 0.35% human serum albumin adjusted to a pH of about 6.5. A sample is frozen at about $-20$ C. for later testing of mitogenic activity Another sample is streaked onto blood agar as a sterility test.

The platelet rich plasma is the only blood fraction utilized in the processes and compositions of the invention. The PRP is then activated with purified thrombin at a rate of about 1 to about 10 units of thrombin per milliliter of PRP. Preferably, about 1 unit of thrombin per ml of platelet-rich plasma is utilized. The activity of the thrombin coagulates the fibrinogen and activates platelets causing them to release alpha granules containing platelet-derived growth factor and platelet-derived angio-genesis factor. The thrombin used was Thrombinar TM brand from Armour Pharmaceutical Co. of Kankakee, Ill. The platetlets and thrombin are allowed to incubate at room temperature for about 5-10 minutes.

The PRP is then subjected to a removal of platelets and fibrin by centrifugation. The resulting supernatant contains both PDAF and PDGF after centrifuging at 950 x g for about 5 minutes at 4 C. The pellet is discarded since the PDAF & PDGF have been extracted into the supernatant. PDGF has been isolated and characterized. It is a protein of 30,000 molecular weight which breaks down into two molecular weight species of 15,000 and 14,000 molecular weight.

In order to apply the PDAF and PDGF in the platelet-free supernatant thus obtained to a wound, it is desirable to utilize a carrier substance which is biologically compatible and acts as a temporary "depot." A macromolecular substance such as microcrystalline collagen provides a suitable carrier. An especially preferred carrier is Avitene ® brand microcrystalline collagen from FMC Corp., Avicel Dept., Marus Hook, PA 19061. The resultant composition is thicker and will tend to remain in position in contact with the wound. Debrisan TM brand wound dressing which contains Sepharose TM brand beads, trademarks of Pharmacia Fine Chemicals, Inc. of Piscataway, N.J., may be utilized as an alternative carrier. Preferably, about 8-10ml of supernatant per gram of carrier is used to produce a paste.

Application of the wound treating composition is by physically applying the material over and into the wound as in applying a medicated salve. Treatments should be repeated on a daily basis as long as the wound remains open, A preferred treatment is to apply an approximately one mm thick dressing of the platelet factor/carrier complex to the wound in the morning. It is then dressed with a sterile, dry dressing. In the evening, the dressing is removed and the substance is removed by washing with sterile saline.

Although the clinical testing involving the wound treating compositions of the invention have been directed to wounds on the body exterior, the compositions may treat internal wounds as well. Sutures may be impregnated with the wound treating compositions to speed internal healing. Alternatively, the composition may be applied over the damaged tissue directly.

Initial clinical trials have been performed on eight patients, all with nonhealing wounds from periods of one to five years. All patients had maximal standardized care in attempts to heal the wounds. That therapy had failed. In all cases, administration of platelet-derived factors initiated a healing response as evidenced by granulation tissue formation (granulation tissue contains ibroblasts, endothelial cells and collagen). The wounds closed by contraction and epithelialization or by skin grafting. Stimulation of healing and eventual repair occurred in all applications.

While it is preferred to prepare activated PRP for wound treatment purposes directly from the injured animal's own blood, the advantages of the invention may be achieved by using blood or outdated platelets from animals of the same species. Utilization of blood from the injured individual to be treated is especially preferred since it avoids exposure to possible hepatitis or other contaminants from banked blood. The use of a patient's own blood would also eliminate any possible allergic reactions. A consistent source of the material may be obtained from washed, outdated human platelets. The substances may also be utilized in veterinary applications by utilizing platelets derived from the animal itself or another animal within the same species.

EXAMPLE I

A patient having an open wound on the left foot following debridement of dead tissue and transmetatarsal amputation was started on PDGF and PDAF, obtained as described above from his own blood. After the treatment protocol, the wound was filled with new granulation tissue. A subsequent debridement showed completely covered metatarsal bones and contracture of the sizable wound.

EXAMPLE II

A patient underwent amputation of his right, great toe and was treated with standard therapy for three weeks without any granulation tissue accumulating within the wound. He was then started on the platelet factor therapy of the invention. After three weeks of treatment, the wound contracted approximately 30-40% and was healing rapidly.

EXAMPLE III

A patient having two large wounds on the medial and lateral aspect of his transmetatarsal amputation stump had been treated for four months without healing, using conventional therapy. Within two weeks of treatment with PDAF and PDGF as described above, the wound had cleared of an apparent infection and started producing granulation tissue.

Thirty-eight nonhealing ulcers from 28 diabetic patients were treated with the PRP paste. The average duration of the ulcers before treatment was 6½ years. A paste prepared from PRP at a concentration of about 10⁹ platelets/ml was combined with Avitene brand collagen. The patients applied the PDGF and PDAF containing paste daily for 12-hour periods for an average of 8 weeks. Each day, the wounds were debrided of dead tissue. All of the wounds produced granulation tissue and closed an average of 83% when compared to starting wound area. Ninety five percent of the ulcers were successfully treated, resulting in either total wound epithlialization or successful skin grafting. Only two of these nonhealing wounds did not heal. The healed ulcers remain closed with no evidence of hypertrophic scar formation or neoplastic formation.

EXAMPLE IV

A diabetic patient who had received a renal transplant and had had a below the knee amputation ("BKA") was treated with a composition prepared as described above. The composition was applied to the patient s stump, including a portion of tissue containing hair follicles, for a period of approximately 3½ months. After treatment, significant hair growth was observed in the area of treatment with the composition where no hair had previously been observed.

EXAMPLE V

Four patients were treated with a composition prepared as described above, with the exception that the platelet buffer used did not contain human serum albumin.

The first patient was a diabetic who had received a BKA. The stump treated with the composition for approximately 2 months.

The second patient suffered from peripheral vascular disease ("PVD"), had received an in situ bypass and had had one great toe amputated. The amputation site was treated with the composition for approximately 8 1/2 months.

The third patient was a diabetic, had received an in situ bypass, and was treated for an ulcer on the lower leg with the composition for a period of approximately 3 months.

The fourth patient had PVD, had received a renal transplant, had received an in situ bypass and had an unhealed wound treated with the composition for a period of approximately 4-4½ months.

In all four patients, after treatment, significant hair growth was observed in the area of treatment with the composition where no hair had previously been observed.

In considering this invention, it should be remembered that the disclosure is illustrative only, and that the scope of the invention should be determined by the appended claims.

I claim:
1. A method of promoting hair growth comprising:
   releasing material from activated platelets; and applying a composition topically to tissue containing hair follicles, said composition comprising said material released from said activated platelets, said compositions being applied in an amount sufficient to cause growth of hair from said tissue.
2. The method of claim 1 wherein said tissue is human tissue.
3. The method of claim 1 wherein said platelets are isolated from blood prior to release of said material.
4. The method of claim 3 wherein said composition is substantially free of (1) blood or plasma contaminants and (2) platelet ghosts or other material found in platelets but not released by said platelets
5. The method of claim 1 wherein said platelets are mammalian platelets.
6. The method of claim 5 wherein said platelets are human platelets.
7. The method of claim 6 wherein prior to release of said material said platelets were removed from the person whose tissue is being treated.
8. The method of claim 6 wherein prior to release of said material said platelets were removed from a person or persons other than the person whose tissue is being treated.
9. The method of claim 1 wherein said material is released from said platelets by use of an activator selected from the group consisting of thrombin, adenosine diphosphate and collagen.
10. The method of claim 9 wherein said activator is thrombin.
11. The method of claim 1 wherein the concentration of said material in said composition is within the range of concentration eguivalent to the amount of material released from about $10^6$ to about $10^9$ platelets per one milliliter of said composition.

* * * * *